United States Patent [19]

Kajinami

[11] 4,154,726

[45] May 15, 1979

[54] PROCESS FOR MODIFYING THE CELL WALL OF SINGLE-CELL MICROORGANISMS USING PERIODATE IONS

[75] Inventor: Shingo Kajinami, Naperville, Ill.

[73] Assignee: Standard Oil Company (Indiana), Chicago, Ill.

[21] Appl. No.: 888,234

[22] Filed: Mar. 20, 1978

[51] Int. Cl.$^2$ ................................................ A23J 1/18
[52] U.S. Cl. .............................. 260/112 R; 195/5 P; 426/62; 426/656
[58] Field of Search .............. 260/112 R; 426/62, 656

[56] References Cited

U.S. PATENT DOCUMENTS

| | | | |
|---|---|---|---|
| 3,819,610 | 6/1974 | Akin | 260/112 R X |
| 3,891,772 | 6/1975 | Ridgway et al. | 426/656 X |
| 3,903,314 | 9/1975 | Chao | 426/656 |
| 3,960,659 | 6/1976 | Fazakerley | 260/112 R X |
| 3,962,466 | 6/1976 | Nakabayashi | 260/112 R X |
| 3,968,009 | 7/1976 | Tannenbaum et al. | 426/62 X |
| 4,007,088 | 2/1977 | Fenci et al. | 260/112 R X |
| 4,079,048 | 3/1978 | Chao | 260/112 R |

OTHER PUBLICATIONS

Experimental Biochemistry, pp. 6-8, 14-16, 27-29, Clark.

*Primary Examiner*—Howard E. Schaln
*Attorney, Agent, or Firm*—Gregory E. Croft; Arthur G. Gilkes; William T. McClain

[57] ABSTRACT

A method for modifying the cell wall of single-cell microorganisms comprises treating the whole cells with a dilute solution of a source of perhalate ions to oxidize the structural polysaccharides in the cell wall without damaging the internal cellular components. If the treated cells are further treated with a dilute basic solution, the cells can be totally dissolved. The protein materials in this solution can then be recovered to obtain a variety of protein products that are whippable, coagulable, and soluble, etc.

10 Claims, No Drawings

PROCESS FOR MODIFYING THE CELL WALL OF SINGLE-CELL MICROORGANISMS USING PERIODATE IONS

BACKGROUND OF THE INVENTION

1. Field of the Invention

This invention relates to methods of treating single cell microorganisms to recover functional proteins. More particularly, it relates to a method of solubilizing the entire cell to yield a solution from which the various functional cell materials can be recovered.

2. Description of the Prior Art

Single cell protein materials such as yeasts have constituents which are highly desirable for many varied uses, the most important constituent being proteins. For example, spray-dried *Candida utilis* yeast typically contains about 52% protein. This protein is predominently located in the cytoplasmic material within the cell wall. The cell wall itself is for the most part made up of two layers, each of which has a polysaccharide network structure. The outermost layer is mannan, which is a polysaccharide derived from mannose. The inner network is glucan, which is derived from glucose. It is highly desirable to isolate the proteinaceous cell components from the others to obtain a concentrate or isolate material, or fractions thereof, which can be used in a variety of food applications.

Aside from nutritional uses for which protein materials have obvious utility, food uses for single cell protein materials are generally determined by their exhibition of certain desirable properties, commonly referred to broadly as "functionality." The functionality of a material is exhibited by the ability of the material to alter the characteristics of the food product into which the material is incorporated. These materials may enhance certain flavors such as cheese, meat, chocolate, etc., or they may alter other physical properties such as whippability, coagulability, color, texture, etc. In general, much of the functional nature of single-cell materials is associated with the availability of the internal cellular components, particularly the proteinaceous materials. Although whole undamaged cells do exhibit some desirable properties, the functionality of the cell can be greatly enhanced by exposing some of the internal cell contents.

Recovery of the proteins from the whole cell has been typically carried out previously by first breaking open the cell wall by mechanical means and then subjecting the broken cell mass to an extraction. Homogenization of the cells is a common physical method for opening the cells, but such a method is expensive and inefficient.

Satisfactory chemical methods for breaking the cell wall have not been developed, although chemical means for cleaving certain carbohydrates such as sugars and some polysaccharides are known in the art. It is known, for example, that periodate ($IO_4^-$) will oxidize sugars according to the reaction:

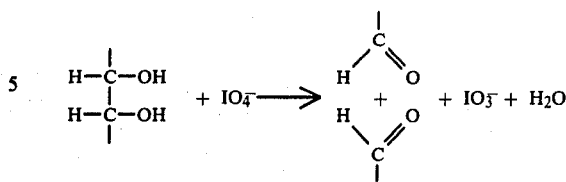

(See "Experimental Biochemistry" pages 6–8, 14–16, 27–29, by John M. Clark, Jr. published by W. H. Freeman and Company, San Francisco and London). This reaction has been used as an analytical tool for determining the structure and polyhydroxyl character of sugars and polysaccharides. However, the applicability of such a method toward recovering proteins from single-cell microorganisms has not been suggested.

It would be desirable to provide a simple chemical means for disrupting the cell wall without any substantial harm to the cell contents. If the cell wall could be perforated, but without being completely broken, the resulting whole cell product would have improved functionality. If the entire cell could be dissolved in an aqueous solution, selected cell components could be readily and selectively recovered by various suitable means such as precipitation or fractionation. Alternatively, because of the large amount of protein present, the cell solution could be used as a starting material for producing a textured product by extruding the solution into an acid bath to precipitate the proteins and form a textured extrudate.

Therefore it is an object of this invention to provide a mild treatment for modifying the cell wall of single-cell microorganisms.

It is a further object of this invention to provide a method for recovering protein material from single-cell microorganisms without resorting to mechanical breakage of the cell wall.

It is another object of this invention to provide a method for completely dissolving the entire cell in an aqueous solution.

These and other objects will become apparent from further reading of this specification.

SUMMARY OF THE INVENTION

It has now been found that functional protein materials can be made readily available for recovery from single-cell microorganisms by treating the cells with an aqueous source of perhalate ions for a time sufficient to permit the entire cell to be dissolved in a dilute basic solution, but not so long as to significantly oxidize the intracellular materials. The treated cells still retain their cellular structure after the perhalate treatment. The proper treatment conditions can be readily determined by those skilled in the art by routine experimentation after reading the teachings of this specification. The most advantageous perhalates are $NaClO_4$, $NaBrO_4$, and $NaIO_4$, with $NaIO_4$ being preferred. The periodates are preferred in the process of this invention because iodine is the weakest oxidizing agent of the more common halogens. This is desirable from the standpoint of achieving control over the oxidation process so as not to oxidize the proteins in addition to oxidizing the cell wall. The other perhalates can be used to achieve faster results if desired, but controlling the extent of reaction is more difficult than when using the periodate ion.

More specifically the invention resides in a method for modifying the cell wall of single-cell microorganisms comprising treating the cells with a dilute solution of a periodate source at a temperature of from about 15° C. to about 40° C. for at least about 7 hours and preferably from about 7 to about 24 hours. The treated cells can be separated from the treating solution by any suitable means such as filtration or centrifugation. The periodates, such as the alkali periodates for example, have been found to be particularly effective in oxidizing the structural polysaccharides of the cell wall and yet are not so harsh so as to oxidize and therefore damage the proteins within the cell. To effectively break down the cell wall with a minimal effect on the cell contents, the concentration of the aqueous periodate solution must nevertheless be dilute, that is to say from about 0.01 N to about 1 N, and preferably in the range of about 0.1 N to about 0.5 N.

The treatment temperature and times are inversely related with the higher treatment temperatures requiring relatively shorter treatment times. An advantageous temperature range generally is from about 15° C. to about 40° C. with a treatment time of at least about 7 hours and preferably not more than 24 hours. The limitations of time and temperature are governed by the effect of the treatment on the cell contents and upon the ability of the entire cell to be subsequently dissolved in a dilute basic solution. Temperatures exceeding about 40° C. may have a damaging effect by oxidizing the protein molecules within the cell wall. Correspondingly, long treatment times may also have the same effect. This will not be as critical if the treated cells are intended to be used as a functional whole cell product, but if dissolution of the cells, as set forth below, is desired to recover the internal cellular components, then it is very important not to overtreat with the perhalate ion solution. Conversely, treatment temperatures below 15° C. require such a long treatment time that such conditions are not deemed to be practical, although such temperatures and treatment times outside the above said ranges are still within the scope of this invention. There is a wide latitude in determining the proper conditions for a particular system and these conditions can be readily determined by one skilled in the art by routing experimentation after reading this specification.

The treated cells can be separated from the treating solution by any suitable means such as centrifugation or filtration and the separated cells can be used as a functional whole cell product. Preferably, however, the separated cells are dissolved in a hot dilute basic solution at a temperature of preferably at least about 40° C. Total dissolution of the cells is a very unexpected result. The higher temperatures facilitate faster dissolution of the cells, whereas those below 40° C. act very slowly and are not preferable. The strength of the dilute aqueous basic solution should be from about 0.01 N to about 2 N, with 0.1 N to about 1 NaOH being preferred.

This process provides a solution of all the cell components which can be further processed to give a wide variety of products, such as products which are whippable, coagulable, soluble, etc. Specifically, the dissolved cell solution can be acidified with any suitable acid, such as hydrochloric acid, to precipitate proteins at their isoelectric point, which generally occurs between a pH of from about 3 to about 4. The precise pH used can be selected to precipitate particular proteins as desired. The precipitated proteins can then be recovered by partitioning, such as filtration or centrifugation, and used in a wide variety of food applications well know to those skilled in the art.

DESCRIPTION OF THE PREFERRED EMBODIMENTS

The following specific examples will serve to illustrate the basis for this invention.

EXAMPLE 1

About 300 mg. of spray dried yeast cells of *Candida utilis* grown on an ethanol substrate were placed in 5 ml. of 0.5 N $NaIO_4$ solution for 24 hours at 37° C. The treated cells became "clumpy" but still retained their cellular organization as viewed under a microscope. The supernatant treating solution was decanted and the treated cells were washed with water and soaked in 10 ml. of fresh water for 24 hours to remove as much $IO_4$ and $IO_3$ as possible. The water was then decanted and the washed cells were placed in a 1 N NaOH solution and heated until the cells dissolved to form a clear solution. Dissolving the entire cell was an unexpected result. Acidification of the cell solution to a pH 3–4 caused precipitation and coagulation of white protein-like cell materials. Generally, about 10–40 weight percent of the cell material remains in solution after precipitation.

EXAMPLE 2

The procedure of Example 1 was repeated except that untreated live cells (instead of spray dried cells) were treated with 0.5 N $NaIO_4$ at room temperature for 24 hours. These cells also dissolved to form a clear solution from which a white protein-like precipitate formed upon acidification as in Example 1.

EXAMPLE 3

The procedure of Example 1 was repeated, except the $NaIO_4$ treated cells were placed in a dilute hot acid solution (0.1 n HCl) instead of a dilute hot basic solution. The cells did not dissolve and retained some cellular organization, although they were much more deformed than were the $NaIO_4$ treated cells prior to the acid treatment. This method provides a whole cell product which may have increased functionality in food applications.

These examples are shown for purposes of illustration and it will be obvious to those skilled in the art that many variations can be made without departing from the scope of this invention.

I claim:

1. A method for dissolving single-cell microorganisms comprising treating the cells with a dilute source of periodate ions and dissolving the treated cells in a dilute basic solution.

2. The method of claim 1 wherein the source of periodate ions is a dilute solution of $NaIO_4$.

3. The method of claim 1 wherein proteins within the dissolved cell solution are precipitated by acidification and separated.

4. The method of claim 1 wherein the single-cell microorganism is a yeast.

5. The method of claim 1 wherein the single-cell microorganism is *Candida utilis* yeast.

6. A method for treating *Candida utilis* yeast cells comprising:
   (a) treating the yeast cells in a dilute solution of $NaIO_4$ at a temperature of from about 15° C. to about 40° C. for at least about 7 hours; and (b) partitioning the treated yeast cells from the NaIO₄ solution.

7. The method of claim 6, wherein the partitioned cells are dissolved in a dilute basic solution.

8. The method of claim 7 wherein the dilute basic solution dissolves the cells at from about 40° C. to about 90° C.

9. The method of claim 6 wherein the yeast cells are treated with a solution of about 0.5N NaIO₄ at a temperature of about 37° C. for about 24 hours.

10. The method of claim 9 wherein the partitioned yeast cells are dissolved in about 1N hot NaOH.

* * * * *

UNITED STATES PATENT OFFICE
CERTIFICATE OF CORRECTION

Patent No. 4,154,726　　　　　　　　　　　　Dated May 15, 1979

Inventor(s) Shingo Kajinami

It is certified that error appears in the above-identified patent and that said Letters Patent are hereby corrected as shown below:

| Patent Column | Line | |
|---|---|---|
| 3 | 44 | "routing" should be --routine-- |
| 3 | 57 | "1 NaOH" should be --1 N NaOH-- |
| 4 | 39 | "0.1 n HCl" should be --0.1 N HCl-- |

Signed and Sealed this

Sixth Day of November 1979

[SEAL]

Attest:

RUTH C. MASON  
Attesting Officer

LUTRELLE F. PARKER  
Acting Commissioner of Patents and Trademarks